United States Patent
Li et al.

(10) Patent No.: US 10,020,191 B2
(45) Date of Patent: Jul. 10, 2018

(54) METHOD FOR CHARACTERIZING CARBON NANOTUBES BY USING SCANNING ELECTRON MICROSCOPE

(71) Applicants: Tsinghua University, Beijing (CN); HON HAI PRECISION INDUSTRY CO., LTD., New Taipei (TW)

(72) Inventors: Dong-Qi Li, Beijing (CN); Yang Wei, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 15/661,061

(22) Filed: Jul. 27, 2017

(65) Prior Publication Data
US 2018/0118563 A1  May 3, 2018

(30) Foreign Application Priority Data
Oct. 31, 2016 (CN) .......................... 2016 1 0933463

(51) Int. Cl.
- *H01L 21/02* (2006.01)
- *B82B 3/00* (2006.01)
- *G01N 23/2251* (2018.01)
- *H01L 51/00* (2006.01)

(52) U.S. Cl.
CPC ...... *H01L 21/02606* (2013.01); *B82B 3/0071* (2013.01); *G01N 23/2251* (2013.01);
(Continued)

(58) Field of Classification Search
CPC .......... H01L 21/02606; H01L 51/0048; B82B 3/0014; B82B 3/0071; B82B 3/009;
(Continued)

(56) References Cited

U.S. PATENT DOCUMENTS

| | | | |
|---|---|---|---|
| 7,378,075 B2 | 5/2008 | Someya et al. | |
| 8,900,709 B2 * | 12/2014 | Jiang | B82Y 10/00 423/448 |

(Continued)

OTHER PUBLICATIONS

Li Jie et al., Direct Identification of Metallic and Semiconducting Single-walled Carbon Nanotubes in Scanning Electron Microscopy, Nano Letters, Jun. 25, 2012, 4095-4101, 12.

*Primary Examiner* — Stephen W Smoot
(74) *Attorney, Agent, or Firm* — ScienBiziP, P.C.

(57) ABSTRACT

A method for characterizing carbon nanotubes comprising: providing a conductive substrate and applying an insulating layer on the conductive substrate; forming a carbon nanotube structure on a surface of the insulating layer, the carbon nanotube structure includes at least one carbon nanotube; placing the carbon nanotube structure under a scanning electron microscope, adjusting the scanning electron microscope with an accelerating voltage ranging from 5~20 KV, a dwelling time ranging 6~20 microseconds and a magnification ranging from 10000~100000 times; taking photos of the carbon nanotube structure with the scanning electron microscope; and, obtaining a photo of the carbon nanotube structure, the photo shows the at least one carbon nanotube and a background.

13 Claims, 5 Drawing Sheets

(52) U.S. Cl.
CPC ...... *C01B 2202/08* (2013.01); *H01L 51/0048* (2013.01); *Y10S 977/742* (2013.01); *Y10S 977/852* (2013.01); *Y10S 977/881* (2013.01)

(58) Field of Classification Search
CPC . B82Y 35/00; C01B 2202/08; C01P 2004/03; C01P 2004/13; G01N 23/04; G01N 23/2251; Y10S 977/742; Y10S 977/72; Y10S 977/842; Y10S 977/852; Y10S 977/854; Y10S 977/881
See application file for complete search history.

(56) References Cited

U.S. PATENT DOCUMENTS

| | | | | |
|---|---|---|---|---|
| 2005/0207964 A1* | 9/2005 | Kim | ...................... | B82Y 30/00 423/447.3 |
| 2005/0255613 A1* | 11/2005 | Kim | ...................... | B82Y 10/00 438/20 |
| 2008/0048134 A1* | 2/2008 | Shirai | ...................... | H05G 2/003 250/504 R |
| 2008/0102019 A1* | 5/2008 | Jeong | ...................... | B01J 19/10 423/447.1 |
| 2010/0009183 A1* | 1/2010 | Noguchi | ...................... | C08J 5/04 428/367 |
| 2010/0051881 A1* | 3/2010 | Ahn | ...................... | B82Y 30/00 252/513 |
| 2012/0315429 A1* | 12/2012 | Stamp | ...................... | B29C 70/028 428/72 |
| 2013/0171516 A1* | 7/2013 | Wang | ...................... | H01M 4/663 429/211 |
| 2015/0290620 A1* | 10/2015 | Jones | ...................... | B82Y 30/00 518/703 |
| 2016/0251534 A1* | 9/2016 | Burlett | ...................... | C01B 31/0273 524/574 |

* cited by examiner providing a conductive substrate and applying an insulating layer on the conductive substrate;

↓ forming a carbon nanotube structure on a surface of the insulating layer, the carbon nanotube structure includes at least one carbon nanotube;

↓ placing the carbon nanotube structure under a scanning electron microscope, adjusting the scanning electron microscope with an accelerating voltage ranging from 5~20 KV, a dwelling time ranging 6~20 microseconds and a magnification ranging from 10000~100000 times;

↓ taking photos of the carbon nanotube structure with the scanning electron microscope; and

↓ obtaining a photo of the carbon nanotube structure, the photo shows the at least one carbon nanotube and a background.

FIG. 3

METHOD FOR CHARACTERIZING CARBON NANOTUBES BY USING SCANNING ELECTRON MICROSCOPE

CROSS-REFERENCE TO RELATED APPLICATIONS

This application claims all benefits accruing under 35 U.S.C. § 119 from China Patent Application No. 201610933463.2, filed on Oct. 31, 2016, in the China Intellectual Property Office, the contents of which are hereby incorporated by reference.

FIELD

The present disclosure relates to a method for characterizing carbon nanotubs.

BACKGROUND

Single-walled carbon nanotubes are a kind of nanomaterial with great potential for research. Based on its nanoscale size and special structure, single-walled carbon nanotubes have good electrical properties, photoelectric properties and semiconductor-type properties. Single-walled carbon nanotubes can be divided into two types: metallic type and semiconducting type. Because of the different application of these two types of single-walled carbon nanotubes, they need to be distinguished. With the application of carbon nanotubes more and more widely, how to distinguish metallic carbon nanotubes and semiconducting carbon nanotubes become a hot research.

Conventional methods for distinguishing metallic carbon nanotubes and semiconducting carbon nanotubes include Raman spectroscopy or electrical measurement methods. The complexity of the operation of these methods lead to lower efficiency. Scanning electron microscopy, because of its high discrimination efficiency, more and more people use it to characterize carbon nanotubes. Referring to FIGS. 1 and 2, in the conventional method of characterizing carbon nanotubes using a scanning electron microscope, a lower (1 kV or so) accelerating voltage is used in order to obtain a clear and high contrast photograph. In the carbon nanotube photo obtained by the traditional scanning electron microscope characterization method, the electrical conductivity of carbon nanotubes is related to the color of the carbon nanotubes in the photo. The lighter the color, the better the electrical conductivity. However, the color of all the carbon nanotubes including the metallic carbon nanotubes and the semiconducting carbon nanotubes is lighter than the color of the photo background. When the metallic carbon nanotubes and the semiconducting carbon nanotubes are both present in the photo, it is very hard to distinguish the carbon nanotubes having middle color, such as gray carbon nanotubes. Therefore, the accuracy of the traditional scanning electron microscopy method for characterizing carbon nanotubes in the identification of carbon nanotubes species is not high enough. Moreover, since the color of both the metallic carbon nanotubes and the semiconducting carbon nanotubes displayed in the photo is lighter than the photo background color, when there is only one type of carbon nanotubes in the photo, it is difficult to judge that the carbon nanotubes in the photo are metallic carbon nanotubes or semiconducting carbon nanotubes.

What is needed, therefore, is to provide a method for characterizing carbon nanotubes that can overcome the above disadvantages.

BRIEF DESCRIPTION OF THE DRAWINGS

Implementations of the present technology will now be described, by way of example only, with reference to the attached figures, wherein:

FIG. 3 is a chart flow showing a method for characterizing carbon nanotubes according to one embodiment.

DETAILED DESCRIPTION

Figure 1:
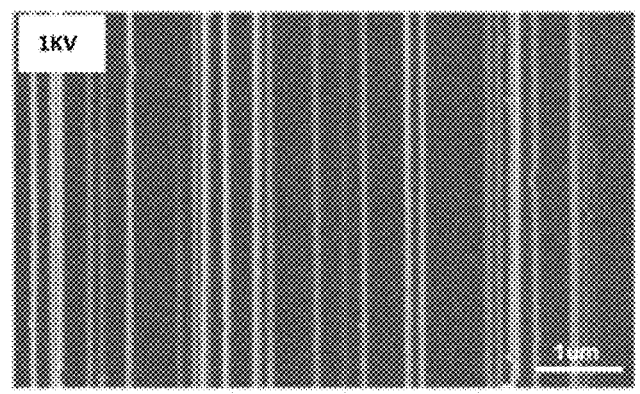
FIG. 1 is a photo of carbon nanotubes obtained by traditional scanning electron microscope characterization method.
Figure 2:
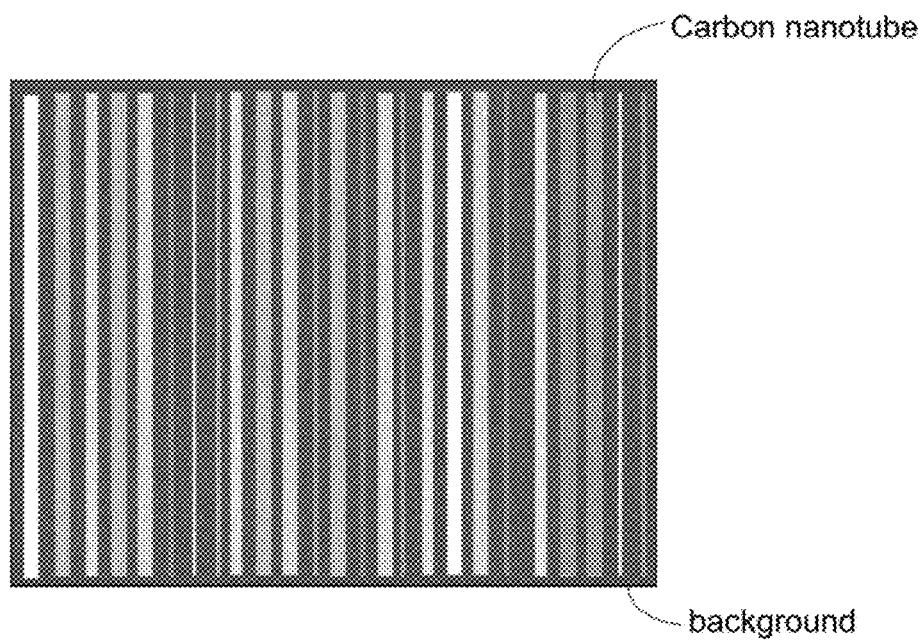
FIG. 2 is a structure schematic view of FIG. 1.

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean "at least one."

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts have been exaggerated to illustrate details and features of the present disclosure better.

Several definitions that apply throughout this disclosure will now be presented.

The term "substantially" is defined to be essentially conforming to the particular dimension, shape, or other feature which is described, such that the component need not be exactly or strictly conforming to such a feature. The term "comprise," when utilized, means "include, but not necessarily limited to"; it specifically indicates open-ended inclusion or membership in the so-described combination, group, series, and the like.

Referring to FIG. 3, one embodiment is described in relation to a method for characterizing carbon nanotubes. The method for characterizing carbon nanotubes includes steps of:

S1: providing a conductive substrate and applying an insulating layer on the conductive substrate;

S2: forming a carbon nanotube structure on a surface of the insulating layer, the carbon nanotube structure includes at least one carbon nanotube;

S3: placing the carbon nanotube structure under a scanning electron microscope, adjusting the scanning electron microscope with an accelerating voltage ranging from 5~20 KV, a dwelling time ranging 6~20 microseconds and a magnification ranging from 10000~100000 times; and taking photos of the carbon nanotube structure with the scanning electron microscope; and S4: obtaining a photo of the carbon nanotube structure, the photo shows the at least one carbon nanotube and a background.

In step S1, a material of the conductive substrate is not limited, as long as it is a conductive material. The material of the conductive substrate can be metal, conductive organic material, or a doped conductive material. In the present embodiment, the material of the conductive substrate is doped silicon. A material of the insulating layer can be oxide or polymer material. In the present embodiment, the material of the insulating layer silicon oxide. A thickness of the insulating layer ranges from 50 nanometers to 300 nanometers.

In step S2, the carbon nanotube structure comprises one carbon nanotube or a plurality of carbon nanotubes. If the carbon nanotube structure includes a plurality of carbon nanotubes, the plurality of carbon nanotubes can be parallel to the surface of the insulating layer. If the carbon nanotube structure comprises a plurality of carbon nanotubes, the plurality of carbon nanotubes can include metallic carbon nanotubes and/or semiconducting carbon nanotubes. In the present embodiment, the carbon nanotube structure includes a plurality of metallic carbon nanotubes and a plurality of semiconducting carbon nanotubes.

In step S3, in some embodiments, the accelerating voltage is 15~20 kV and the dwelling time is 10~20 microseconds. In the present embodiment, the acceleration voltage is 10 kV, the dwelling time is 20 microseconds, and the magnification is 20,000 times.

Figure 4:
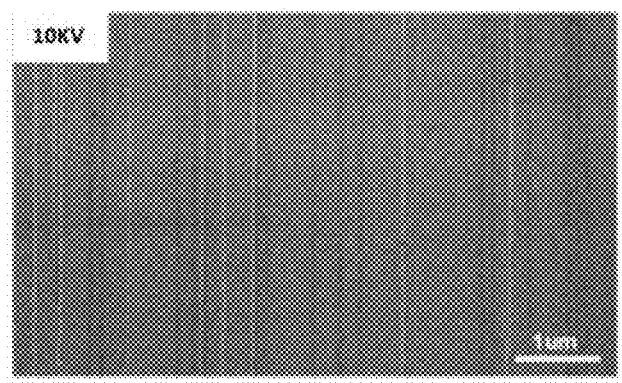
FIG. 4 is a photo of carbon nanotubes obtained by a method for characterizing carbon nanotubes according to one embodiment.
Figure 5:
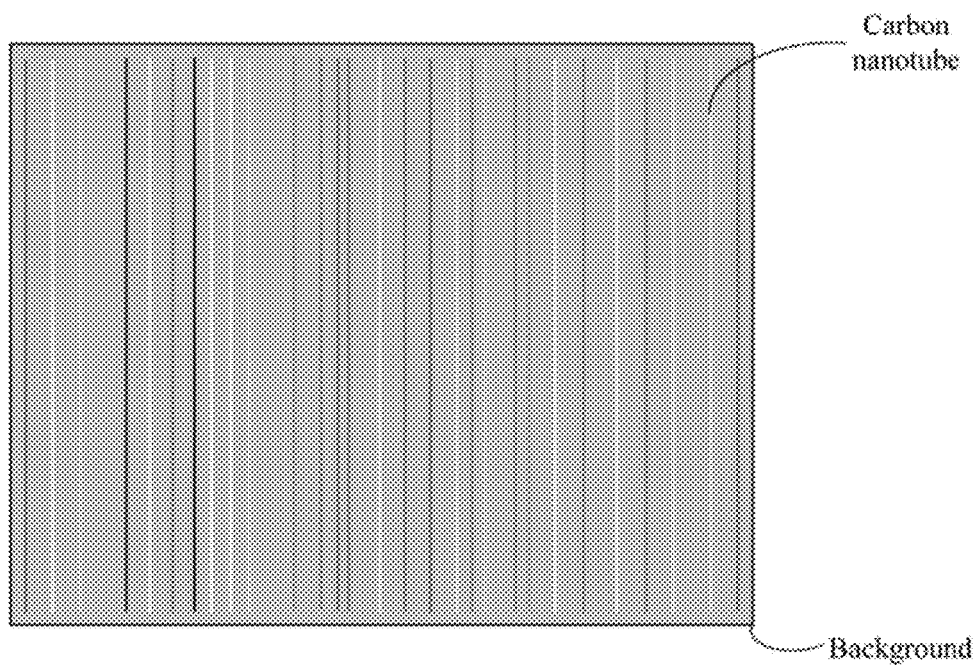
FIG. 5 is a structure schematic view of FIG. 4.

In step S4, a photo of the carbon nanotube structure is obtained as shown in FIG. 4, and the schematic view thereof is shown in FIG. 5. FIGS. 4 and 5 show a background and an image of the plurality of carbon nanotubes in the carbon nanotube structure. As can be seen from FIGS. 4 and 5, the color of some carbon nanotubes is lighter than the color of the background, and the color of some carbon nanotubes is deeper than the color of the background. The carbon nanotubes with lighter color than the background are metallic carbon nanotubes. The carbon nanotubes with deeper color than the background are semiconducting carbon nanotubes.

Compared FIG. 1 obtained by the traditional method for characterizing carbon nanotubes by scanning electron microscopy with FIG. 4 obtained by the method for characterizing carbon nanotubes of the present disclosure, the method for characterizing carbon nanotubes of the present disclosure has the many advantages. The advantages are listed below.

In the carbon nanotube photo obtained by the traditional scanning electron microscope characterization method, the color of all the carbon nanotubes including metallic carbon nanotubes and semiconducting carbon nanotubes, is lighter than the color of the photo background. When the metallic carbon nanotubes and the semiconducting carbon nanotubes are both present in the photo, it is very hard to distinguish the type of carbon nanotubes having middle color, such as gray carbon nanotubes. Therefore, the accuracy of the traditional scanning electron microscopy method for characterizing carbon nanotubes in the identification of carbon nanotubes types is not high enough. However, in carbon nanotube photo obtained by the method for characterizing carbon nanotubes according to present disclosure, the color of metallic carbon nanotubes is lighter than the color of the background, and the color of semiconducting carbon nanotubes is deeper than the color of the background. As such, metallic carbon nanotubes and semiconducting carbon nanotubes can be distinguished quickly and without mistake.

Further, in the carbon nanotube photo obtained by the traditional scanning electron microscope characterization method, the color of both the metallic carbon nanotubes and the semiconducting carbon nanotubes displayed in the photo is lighter than the photo background color, when there is only one type of carbon nanotubes in the photo, it is difficult to judge that the carbon nanotubes in the photo are metallic carbon nanotubes or semiconducting carbon nanotubes. However, in carbon nanotube photo obtained by the method for characterizing carbon nanotubes according to present disclosure, the color of metallic carbon nanotubes is lighter than the color of the background, and the color of semiconducting carbon nanotubes is deeper than the color of the background. As such, even if there is a single type of carbon nanotubes, the type of carbon nanotubes can be distinguish quickly and without mistake.

Further more, compared with FIG. 4, the contrast of FIG. 1 is higher, the carbon nanotubes are visually more easily observed, and the photo is more beautiful. However, the photo obtained in the embodiment of the present disclosure is relatively low in contrast, and the photo is also relatively not beautiful. As such, in order to get the photo like FIG. 1, lower (1 kV or less than that) accelerating voltage is used in the existing technology to characterize carbon nanotubes. As such, the present disclosure provides a method for characterizing carbon nanotubes overcoming technical bias and capable of accurately judging the types of carbon nanotubes.

Moreover, compared with FIG. 1, a width of the carbon nanotube in the photo is relatively small, and therefore, the method for characterizing carbon nanotube provided by the present disclosure is more suitable for characterizing carbon nanotubes having a higher density.

It is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

Depending on the embodiment, certain of the steps of a method described may be removed, others may be added, and the sequence of steps may be altered. The description and the claims drawn to a method may include some indication in reference to certain steps. However, the indication used is only to be viewed for identification purposes and not as a suggestion as to an order for the steps.

What is claimed is:

1. A method for characterizing carbon nanotubes comprising:
   providing a conductive substrate and applying an insulating layer on the conductive substrate;
   forming a carbon nanotube structure on a surface of the insulating layer, the carbon nanotube structure includes at least one carbon nanotube;
   placing the carbon nanotube structure under a scanning electron microscope, adjusting the scanning electron microscope with an accelerating voltage ranging from 5~20 KV, a dwelling time ranging from 6~20 microseconds and a magnification ranging from 1000~100000 times;
   taking photos of the carbon nanotube structure with the scanning electron microscope; and
   obtaining a photo of the carbon nanotube structure, the photo shows the at least one carbon nanotube and a background.

2. The method of claim 1, wherein a material of the conductive substrate is metal, conductive organic material, or a doped conductive material.

3. The method of claim 1, wherein a material of the conductive substrate is doped silicon, and a material of the insulating layer is silicon oxide.

4. The method of claim 1, wherein a material of the insulating layer is oxide or polymer material.

5. The method of claim 4, wherein a thickness of the insulating layer ranges from 50 nanometers to 300 nanometers.

6. The method of claim 1, wherein the carbon nanotube structure is a single carbon nanotube.

7. The method of claim 1, wherein the carbon nanotube structure comprises a plurality of carbon nanotubes.

8. The method of claim 7, wherein the plurality of carbon nanotubes comprises a plurality of metallic carbon nanotubes and a plurality of semiconducting carbon nanotubes.

9. The method of claim 7, wherein the plurality of carbon nanotubes are parallel with a surface of the insulating layer.

10. The method of claim 1, wherein the accelerating voltage is ranged from 15 KV to 20 kV.

11. The method of claim 1, wherein the dwelling time is in a range from 10 microseconds to 20 microseconds.

12. The method of claim 1, wherein the photo shows a background and an image of the carbon nanotube structure.

13. The method of claim 12, wherein the carbon nanotube structure comprise a plurality of metallic carbon nanotubes with a color lighter than a color of the background and a plurality of semiconducting carbon nanotubes with a color deeper than the color of the background.

* * * * *